United States Patent [19]
Dubief et al.

[11] Patent Number: 6,165,444
[45] Date of Patent: Dec. 26, 2000

[54] COMPOSITION FOR TREATING KERATINOUS MATERIAL, INCLUDING AT LEAST ONE SILICONE-GRAFTED POLYMER AND AT LEAST ONE FATTY-CHAIN AMIDE, AND USES THEREOF

[75] Inventors: Claude Dubief, Le Chesnay; Daniele Cauwet-Martin; Christine Dupuis, both of Paris, all of France

[73] Assignee: L'Oreal, Paris, France

[21] Appl. No.: 08/983,335

[22] PCT Filed: Sep. 16, 1996

[86] PCT No.: PCT/FR96/01437

§ 371 Date: Dec. 30, 1997

§ 102(e) Date: Dec. 30, 1997

[87] PCT Pub. No.: WO97/12587

PCT Pub. Date: Apr. 10, 1997

[30] Foreign Application Priority Data

Sep. 29, 1995 [FR] France .................................. 95 11484

[51] Int. Cl.⁷ ...................................................... A61K 9/12
[52] U.S. Cl. .......................... 424/45; 424/47; 424/70.11
[58] Field of Search ................................ 528/30; 424/45, 424/47, 70.11, DIG. 1, DIG. 2, 70.12; 514/63, 957

[56] References Cited

U.S. PATENT DOCUMENTS

| 5,380,455 | 1/1995 | Tsuda et al. ........................ 252/174.23 |
|---|---|---|
| 5,840,291 | 11/1998 | Tsubakihara et al. ............. 424/70.122 |
| 5,869,034 | 2/1999 | Montastier et al. ................. 424/78.03 |
| 5,879,671 | 3/1999 | Halloran et al. .................. 424/70.122 |
| 5,911,979 | 6/1999 | Midha et al. ........................ 424/70.12 |
| 5,919,439 | 7/1999 | Torgerson et al. ................ 424/70.122 |

FOREIGN PATENT DOCUMENTS

| 0 412 707 | 2/1991 | European Pat. Off. . |
|---|---|---|
| 0 453 683 | 10/1991 | European Pat. Off. . |
| 0 455 429 | 11/1991 | European Pat. Off. . |
| 0 521 647 | 1/1993 | European Pat. Off. . |
| 0 581 152 | 2/1994 | European Pat. Off. . |
| 2 679 770 | 2/1993 | France . |
| 09/03704 | 3/1993 | WIPO . |

*Primary Examiner*—Thurman K. Page
*Assistant Examiner*—A. Pulliam
*Attorney, Agent, or Firm*—Finnegan, Henderson, Farabow, Garrett & Dunner, L.L.P.

[57] ABSTRACT

A cosmetic or dermatological composition for treating keratinous material, particularly human hair, including a cosmetically or dermatologically acceptable medium containing at least one silicone-grafted polymer with a polysiloxane portion and a portion consisting of a non-silicone organic chain, wherein one of the two portions constitutes the main polymeric chain while the other is grafted onto said main chain, an at least one selected fatty-chain amide. Such compositions are particularly suitable for use as rinsable or non-rinsable products for washing and conditioning hair, hair setting or hair styling.

55 Claims, No Drawings

COMPOSITION FOR TREATING KERATINOUS MATERIAL, INCLUDING AT LEAST ONE SILICONE-GRAFTED POLYMER AND AT LEAST ONE FATTY-CHAIN AMIDE, AND USES THEREOF

The present invention relates to a cosmetic or dermatological composition for treating keratin substances, in particular human hair, this composition comprising at least one grafted silicone polymer comprising a polysiloxane portion and a portion consisting of a non-silicone organic chain, one of the two portions constituting the main chain of the polymer, the other being grafted onto the said main chain, and at least one selected fatty-chain amide, as well as to their uses.

Washing and/or care and/or treatment compositions for the hair containing styling polymers in their formulation generally have the drawback of making it difficult to disentangle, restyle or brush the hair. Moreover, the styling properties such as the fixing power are still unsatisfactory.

The expression fixing power of the composition will be understood to refer to the ability of this composition to give the hair cohesion such that the initial shape of the hairstyle is held.

The Applicant has discovered, surprisingly, that using compositions containing a styling polymer of the grafted silicone polymer type comprising a polysiloxane portion and a portion consisting of a non-silicone organic chain, one of the two portions constituting the main chain of the polymer, the other being grafted onto the said main chain of the polymers of the grafted silicone polymer type, in combination with particular fatty-chain amides, improves the fixing power, the disentangling and the styling or brushing of the hair after it has been applied.

These compositions also make it possible to enhance the cosmetic properties, in particular the softness and smoothness of the hair.

The composition according to the invention is thus essentially characterized in that it contains, in a cosmetically or dermatologically acceptable medium, at least one grafted silicone polymer comprising a polysiloxane portion and a portion consisting of a non-silicone organic chain, one of the two portions constituting the main chain of the polymer, the other being grafted onto the said main chain, and at least one fatty-chain amide corresponding to the general formula (I):

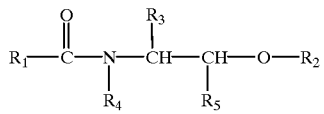

in which:
R$_1$ denotes either a linear or branched, saturated or unsaturated, C$_9$–C$_{30}$ hydrocarbon radical, it being possible for this radical to be substituted with one or more hydroxyl groups optionally esterified with a saturated or unsaturated C$_{16}$–C$_{30}$ fatty acid; or a radical R''—(NR—CO)$_n$—R' in which n is equal to 0 or 1, R denotes hydrogen or hydroxyethyl, R' and R'' are hydrocarbon radicals the sum of whose carbon atoms is between 9 and 30, R' being a divalent radical;

R$_2$ denotes a hydrogen atom or a (glycosyl)$_n$, (galactosyl)$_m$ or sulphogalactosyl radical, in which n is an integer ranging from 1 to 4 and m is an integer ranging from 1 to 8;

R$_3$ denotes a hydrogen atom or a saturated or unsaturated, C$_{16}$–C$_{27}$ hydrocarbon radical, it being possible for this radical to be substituted with one or more C$_1$–C$_{14}$ alkyl radicals; R$_3$ can also denote a C$_{15}$–C$_{26}$ α-hydroxyalkyl radical, the hydroxyl group optionally being esterified with a C$_{16}$–C$_{30}$ α-hydroxy acid;

R$_4$ denotes a hydrogen atom, a C$_1$–C$_4$ alkyl radical, a saturated or unsaturated C$_{16}$–C$_{27}$ hydrocarbon radical or a group —CH$_2$—CHOH—CH$_2$—O—R$_6$ in which R$_6$ denotes a C$_{10}$–C$_{26}$ hydrocarbon radical;

R$_5$ denotes a hydrogen atom or a mono- or polyhydroxylated C$_1$–C$_4$ hydrocarbon radical.

Among the compounds of formula (I), the ceramides and/or glycoceramides whose structure is described by Downing in the Journal of Lipid Research Vol. 35, 2060–2068, 1994, or those described in French patent application FR-2,673,179, the teachings of which are included herein by way of reference, are preferred.

The ceramides more particularly preferred according to the invention are the compounds of formula (I) for which R$_1$ denotes a saturated or unsaturated alkyl derived from C$_{16}$–C$_{22}$ fatty acids, R$_2$ denotes a hydrogen atom and R$_3$ denotes a saturated, linear, C$_{15}$ radical.

Such compounds are, for example:

N-linoleoyldihydrosphingosine,

N-oleoyldihydrosphingosine,

N-palmitoyldihydrosphingosine,

N-stearoyldihydrosphingosine,

N-behenoyldihydrosphingosine, or mixtures of these compounds.

Specific mixtures can also be used, such as, for example, mixtures of ceramide(s) 2 and ceramide(s) 5.

The compounds of formula (I) for which R$_1$ denotes a saturated or unsaturated alkyl radical derived from fatty acids, R$_2$ denotes a galactosyl or sulphogalactosyl radical and R$_3$ denotes a —CH=CH— (CH$_2$)$_{12}$—CH$_3$ group can also be used.

By way of example, mention may be made of the product consisting of a mixture of glycoceramides, sold under the tradename Glycocer by the company Waitaki International Biosciences.

The compounds of formula (I) described in patent applications EP-A-0,227,994 and WO 94/07844 can also be used.

Such compounds are, for example, Questamide H (bis(N-hydroxyethyl-N-cetyl)malonamide) sold by the company Quest and cetylic acid N-(2-hydroxyethyl)-N-(3-cetyloxy-2-hydroxypropyl)amide.

N-Docosanoyl-N-methyl-D-glucamine described in patent application WO 92/05764 and in patent application WO 94/00402 can also be used.

The amide concentration can range approximately between 0.0001% and 20% by weight relative to the total weight of the composition, and preferably approximately between 0.001 and 10% and even more preferably between 0.005 and 3% by weight.

The grafted silicone polymers according to the invention are preferably chosen from polymers having a non-silicone organic skeleton grafted with monomers containing a polysiloxane, polymers having a polysiloxane skeleton grafted with non-silicone organic monomers and mixtures thereof.

In the following text, in accordance with what is generally accepted, the term silicone or polysiloxane is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding ≡Si—O—Si≡), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, substituted or unsubstituted amine groups, amide groups, acyloxy radicals or acyloxyalkyl radicals, hydroxyalkylamino or aminoalkyl radicals, quaternary ammonium groups, amphoteric or betaine groups, anionic groups such as carboxylates, thioglycolates, sulphosuccinates, thiosulphates, phosphates and sulphates, needless to say this list not being limiting in any way (so-called "organomodified" silicones).

In the following text, in accordance with what is generally accepted, the expression "polysiloxane macromer" is understood to refer to any monomer containing a polysiloxane-type polymer chain in its structure.

The polymers containing a non-silicone organic skeleton grafted with monomers containing a polysiloxane, in accordance with the present invention, consist of an organic main chain formed from organic monomers containing no silicone, on which is grafted, inside the said chain and optionally on at least one of its ends, at least one polysiloxane macromer.

The non-silicone organic monomers constituting the main chain of the grafted silicone polymer can be chosen from monomers containing ethylenic unsaturation which are polymerizable via a radical route, monomers which are polymerizable by polycondensation, such as those forming polyamides, polyesters or polyurethanes, and monomers which involve ring opening, such as those of the oxazoline or caprolactone type.

The polymers containing a non-silicone organic skeleton grafted with monomers containing a polysiloxane, in accordance with the present invention, can be obtained according to any means known to those skilled in the art, in particular by reaction between (i) a starting polysiloxane macromer which is correctly functionalized on the polysiloxane chain and (ii) one or more non-silicone organic compounds, themselves correctly functionalized with a function which is capable of reacting with the functional group(s) borne by the said silicone, forming a covalent bond; a classic example of such a reaction is the radical reaction between a vinyl group borne on one of the ends of the silicone with a double bond of a monomer containing ethylenic unsaturation in the main chain.

The polymers containing a non-silicone organic skeleton grafted with monomers containing a polysiloxane, in accordance with the invention, are more preferably chosen from those described in U.S. Pat. Nos. 4,693,935, 4,728,571 and 4,972,037 and patent applications EP-A-0,412,704, EP-A-0,412,707, EP-A-0,640,105 and WO 95/00578. These are copolymers obtained by radical polymerization starting with monomers containing ethylenic unsaturation and silicone macromers having a terminal vinyl group, or alternatively copolymers obtained by reaction of a polyolefin comprising functionalized groups and a polysiloxane macromer having a terminal function which is reacted with the said functionalized groups.

One particular family of grafted silicone polymers containing a non-silicone organic skeleton which is suitable for carrying out the present invention consists of silicone grafted copolymers comprising:

a) from 0 to 98% by weight of at least one lipophilic monomer (A) of low lipophilic polarity containing ethylenic unsaturation, which is polymerizable via a radical route;

b) from 0 to 98% by weight of at least one polar hydrophilic monomer (B) containing ethylenic unsaturation, which is copolymerizable with the (A)—type monomer(s);

c) from 0.01 to 50% by weight of at least one polysiloxane macromer (C) of general formula:

$$X(Y)_n Si(R)_{3-m} Z_m \quad (II)$$

where:

X denotes a vinyl group which is copolymerizable with the monomers (A) and (B);

Y denotes a divalent bonding group;

R denotes a hydrogen, a $C_1$–$C_6$ alkyl or alkoxy or a $C_6$–$C_{12}$ aryl;

Z denotes a monovalent polysiloxane unit having a number-average molecular weight of at least 500;

n is 0 or 1 and m is an integer ranging from 1 to 3; the percentages being calculated relative to the total weight of the monomers (A), (B) and (C).

These polymers are described, along with processes for their preparation, in U.S. Pat. Nos. 4,693,935, 4,728,571 and 4,972,037 and in patent applications EP-A-0,412,704, EP-A-0,412,707 and EP-A-0,640,105. They have a number-average molecular weight preferably ranging from 10,000 to 2,000,000 and preferably a glass transition temperature Tg or a crystalline melting point Tm of at least −20° C.

As examples of lipophilic monomers (A), mention may be made of acrylic or methacrylic acid esters of $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic or methacrylic acid esters of 1,1-dihydro-perfluoroalkanols or of homologues thereof; acrylic or methacrylic acid esters of ω-hydridofluoroalkanols; acrylic or methacrylic acid esters of fluoroalkyl-sulphoamido alcohols; acrylic or methacrylic acid esters of fluoroalkyl alcohols; acrylic or methacrylic acid esters of fluoroether alcohols; or mixtures thereof. The preferred monomers (A) are chosen from the group consisting of n-butyl methacrylate, isobutyl methacrylate, tert-butyl acrylate, tert-butyl methacrylate, 2-ethylhexyl methacrylate, methyl methacrylate, 2-(N-methylperfluorooctanesulphonamido)-ethyl acrylate and 2-(N-butylperfluorooctane-sulphonamido)ethyl acrylate, and mixtures thereof.

As examples of polar monomers (B), mention may be made of acrylic acid, methacrylic acid, N,N-dimethylacrylamide, dimethylaminoethyl methacrylate, quaternized dimethylaminoethyl methacrylate, (meth)acrylamide, N-t-butylacrylamide, maleic acid, maleic anhydride and semiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam, or mixtures thereof. The preferred monomers (B) are chosen from the group consisting of acrylic acid, N,N-dimethylacrylamide, dimethylaminoethyl methacrylate, quaternized dimethylaminoethyl methacrylate and vinylpyrrolidone, and mixtures thereof.

The preferred polysiloxane macromers (C) of formula (II) are chosen from those corresponding to the general formula (III) below:

$$\text{CHR}^1 = \text{CR}^2 - \overset{\overset{\text{O}}{\|}}{\text{C}} - \text{O} - (\text{CH}_2)_q - (\text{O})_p - \text{Si}(\text{R}^3)_{3-m} - (\text{O} - \underset{\underset{\text{CH}_3}{|}}{\overset{\overset{\text{CH}_3}{|}}{\text{Si}}})_r - \text{R}^4 \qquad (\text{III})$$

in which:

R¹ is hydrogen or —COOH (preferably hydrogen);

R² is hydrogen, methyl or —CH₂COOH (preferably methyl);

R³ is $C_1$–$C_6$ alkyl, alkoxy, or alkylamino, $C_6$–$C_{12}$ aryl or hydroxyl (preferably methyl);

R⁴ is $C_1$–$C_6$ alkyl, alkoxy or alkylamino, $C_6$–$C_{12}$ aryl or hydroxyl (preferably methyl);

q is an integer from 2 to 6 (preferably 3);

p is 0 or 1;

r is an integer from 5 to 700;

m is an integer from 1 to 3 (preferably 1).

The polysiloxane macromers of formula:

$$\text{CH}_2 = \underset{\underset{\text{CH}_3}{|}}{\text{C}} - \overset{\overset{\text{O}}{\|}}{\text{C}} - \text{O} - (\text{CH}_2)_3 - \underset{\underset{\text{CH}_3}{|}}{\overset{\overset{\text{CH}_3}{|}}{\text{Si}}} - \text{O} \left[ \underset{\underset{\text{CH}_3}{|}}{\overset{\overset{\text{CH}_3}{|}}{\text{Si}}} - \text{O} \right]_n \underset{\underset{\text{CH}_3}{|}}{\overset{\overset{\text{CH}_3}{|}}{\text{Si}}} - (\text{CH}_2)_3 - \text{CH}_3$$

with n being an integer ranging from 5 to 700, are more particularly used.

One particular embodiment of the invention consists in using a copolymer which can be obtained by radical polymerization starting with the monomer mixture consisting of:

a) 60% by weight of tert-butyl acrylate;

b) 20% by weight of acrylic acid;

c) 20% by weight of silicone macromer of formula:

$$\text{CH}_2 = \underset{\underset{\text{CH}_3}{|}}{\text{C}} - \overset{\overset{\text{O}}{\|}}{\text{C}} - \text{O} - (\text{CH}_2)_3 - \underset{\underset{\text{CH}_3}{|}}{\overset{\overset{\text{CH}_3}{|}}{\text{Si}}} - \text{O} \left[ \underset{\underset{\text{CH}_3}{|}}{\overset{\overset{\text{CH}_3}{|}}{\text{Si}}} - \text{O} \right]_n \underset{\underset{\text{CH}_3}{|}}{\overset{\overset{\text{CH}_3}{|}}{\text{Si}}} - (\text{CH}_2)_3 - \text{CH}_3$$

with n being an integer ranging from 5 to 700; the weight percentages being calculated relative to the total weight of the monomers.

Another particular embodiment of the invention consists in using a copolymer which can be obtained by radical polymerization starting with the monomer mixture consisting of:

a) 80% by weight of tert-butyl acrylate;

b) 20% by weight of silicone macromer of formula:

$$\text{CH}_2 = \underset{\underset{\text{CH}_3}{|}}{\text{C}} - \overset{\overset{\text{O}}{\|}}{\text{C}} - \text{O} - (\text{CH}_2)_3 - \underset{\underset{\text{CH}_3}{|}}{\overset{\overset{\text{CH}_3}{|}}{\text{Si}}} - \text{O} \left[ \underset{\underset{\text{CH}_3}{|}}{\overset{\overset{\text{CH}_3}{|}}{\text{Si}}} - \text{O} \right]_n \underset{\underset{\text{CH}_3}{|}}{\overset{\overset{\text{CH}_3}{|}}{\text{Si}}} - (\text{CH}_2)_3 - \text{CH}_3$$

with n being an integer ranging from 5 to 700; the weight percentages being calculated relative to the total weight of the monomers.

Another particular family of grafted silicone polymers containing a non-silicone organic skeleton, which is suitable for carrying out the present invention, consists of silicone grafted copolymers which can be obtained by reactive extrusion of a polysiloxane macromer having a terminal reactive function, with a polyolefin-type polymer containing reactive groups which can react with the terminal function of the polysiloxane macromer in order to form a covalent bond allowing grafting of the silicone to the main chain of the polyolefin.

These polymers are described, along with a process for their preparation, in patent application WO 95/00578.

The reactive polyolefins are preferably chosen from polyethylenes or polymers of ethylene-derived monomers such as propylene, styrene, alkylstyrene, butylene, butadiene, (meth)acrylates, vinyl esters or equivalents, containing reactive functions which can react with the terminal function of the polysiloxane macromer. They are chosen more particularly from copolymers of ethylene or of ethylene derivatives and of monomers chosen from those containing a carboxylic function, such as (meth)acrylic acid; those containing an acid anhydride function such as maleic anhydride; those containing an acid chloride function such as (meth)acryloyl chloride; those containing an ester function such as (meth) acrylic acid esters; those containing an isocyanate function.

The silicone macromers are preferably chosen from polysiloxanes containing a functionalized group, at the end of the polysiloxane chain or close to the end of the said chain, chosen from the group consisting of alcohols, thiols, epoxy groups and primary and secondary amines, and more particularly from those corresponding to the general formula:

$$T-(CH_2)_s-Si-[(OSiR^5R^6)_t-R^7]_y \qquad (IV)$$

in which T is chosen from the group consisting of NH₂, NHR', an epoxy, OH, or SH function; R⁵, R⁶, R⁷ and R', independently denote a $C_1$–$C_6$ alkyl, phenyl, benzyl, $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200, 000 and more particularly from 9000 to 40,000.

According to the present invention, the grafted silicone polymer(s) containing a polysiloxane skeleton grafted with non-silicone organic monomers comprise a silicone (or polysiloxane (≡Si—O—)ₙ) main chain on which is grafted, inside the said chain as well as, optionally, on at least one of its ends, at least one organic group containing no silicone.

The polymers containing a polysiloxane skeleton grafted with non-silicone organic monomers, according to the invention, can be existing commercial products or alternatively can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between ≡Si—H groups and vinyl groups CH₂=CH—, or alternatively the reaction between thio functional groups —SH with these same vinyl groups.

Examples of polymers with a polysiloxane skeleton grafted containing non-silicone organic monomers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer containing a polysiloxane skeleton grafted with non-silicone organic monomers, which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical homo- or polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or mixtures thereof.

One family of silicone polymers containing a polysiloxane skeleton grafted with non-silicone organic monomers which is particularly suitable for carrying out the present invention consists of silicone polymers containing in their structure the unit of formula (V) below:

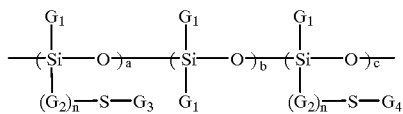

(V)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the homo- or polymerization of at least one anionic monomer containing ethylenic unsaturation; $G_4$ represents a polymer residue resulting from the homo- or polymerization of at least one hydrophobic monomer containing ethylenic unsaturation; m and n are equal to 0 or 1; a is an integer ranging from 0 to 50; b is an integer which may be between 10 and 350; c is an integer ranging from 0 to 50; with the proviso that one of the parameters a and c is other than 0.

Preferably, the unit of formula (V) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the homo- or polymerization of at least one monomer of the carboxylic acid type containing ethylenic unsaturation, preferably acrylic acid and/or methacrylic acid;

$G_4$ represents a polymeric radical resulting from the homo- or polymerization of at least one monomer of the ($C_1$–$C_{10}$) and alkyl (meth)acrylate type and preferably isobutyl and methyl (meth)acrylate.

Examples of silicone polymers corresponding to formula (V) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (V) are, in particular, polydimethylsiloxanes (PDMS) on which are grafted, via a thiopropylene-type connecting chain, polymer units of the polyisobutyl (meth)acrylate type.

Preferably, the number-average molecular mass of the silicone polymers containing a polysiloxane skeleton grafted with non-silicone organic monomers, of the invention, ranges approximately from 10,000 to 1,000,000 and even more preferably approximately from 10,000 to 100,000.

The grafted silicone polymers in accordance with the invention are preferably used in an amount ranging from 0.01 to 20% by weight relative to the total weight of the composition. More preferably, this amount ranges from 0.1 to 15% by weight and even more particularly from 0.5 to 10% by weight.

The grafted silicone polymers according to the invention are preferably chosen from polymers containing a non-silicone organic skeleton grafted with polysiloxane-containing monomers, polymers containing a polysiloxane skeleton grafted with non-silicone organic monomers, and mixtures thereof.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and ispropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

The compositions of the invention are used as rinse-out products or as leave-in products in particular to wash, care for, condition keratin substances such as the hair, maintain the style or shape the style.

These compositions are more particularly hairsetting lotions, blow-drying lotions, fixing compositions (lacquers) and styling compositions. The lotions can be packaged in various forms, in particular in vapourizers, pump-dispenser bottles or in aerosol containers in order to ensure application of the composition in vapourized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for treating keratin substances such as human hair, which consists in applying a composition as defined above to the hair and then optionally in rinsing with water.

The invention will now be illustrated more fully with the aid of the examples which follow, which should not be considered as limiting it to the embodiments described. (In the text which follows, AM means active material.)

EXAMPLES

Example 1

A blow-drying spray of the following composition was prepared:

| | | |
|---|---|---|
| N-Oleoyldihydrosphingosine | | 0.5 g |
| Grafted silicone polymer of formula (V) of polymethyl/methylsiloxane structure containing a 3-propylthio polymethacrylic acid group and 3-propylthio polymethyl methacrylate groups | | 2 g |
| Aminomethylpropanol, 100% neutralization of the said silicone polymer | qs | |
| Ethanol | qs | 100 g |

Example 2

A haircare mousse of the following composition was prepared:

| | | |
|---|---|---|
| N-Oleoyldihydrosphingosine | | 0.5 g |
| Grafted silicone polymer of formula (IV) of polymethyl/methylsiloxane structure containing 3-propylthio polymethacrylic acid groups and 3-propylthio polymethyl methacrylate groups | | 1 g |
| Aminomethylpropanol, 100% neutralization of the said silicone polymer | qs | |
| Copolymer of hydroxyethylcellulose and of diallyldimethylammonium chloride, sold under the trade name Celquat L200 by the company National Starch | | 0.5 g |
| Sorbitan monolaurate oxyethylenated with 20 mol of ethylene oxide (Tween 20 from ICI) | | 0.5 g |
| demineralized water | qs | 100 g |
| Pressurization schema: | | |
| Above composition: | | 90 g |
| Ternary mixture of n-butane, isobutane and propane (23/55/22), sold under the name "Aerogaz 3.2 N" by the company Elf Aquitaine | | 10 g |

When applied to wet hair, this mousse melts rapidly into the hair and improves the disentangling of the wet hair. The dry hair obtained is lively and soft and has good styling properties.

Example 3

A shampoo of the following composition was prepared:

| | | |
|---|---|---|
| Sodium lauryl (C12/C14 70/30) ether sulphate oxyethylenated with 2.2 mol of ethylene oxide1 as an aqueous solution containing 28% AM, sold under the name Empicol ESB 31/F by the company Albright and Wilson | | 16 g AM |
| Grafted silicone polymer of formula (V) of polymethyl/methylsiloxane structure containing 3-propylthio polymethacrylic acid groups and 3-propylthio polymethyl methacrylate groups | | 2 g |
| N-Oleoyldihydrosphingosine | | 0.5 g |
| Fragrance, sequestering agent, preserving agent | | |
| Water | qs | 100 g |

The pH is adjusted to 7 by addition of sodium hydroxide.

Example 4

A rinse-out conditioner of the following composition was prepared:

| | |
|---|---|
| Mixture (80/20 by weight) of cetylstearyl alcohol and of cetylstearyl alcohol oxyethylenated with 33 mol of ethylene oxide | 2 g |
| Grafted silicone polymer of formula (V) of polymethyl/methylsiloxane structure containing 3-propylthio polyisobutyl methacrylate groups in solution in a cyclic volatile silicone | 2 g |
| N-Oleoyldihydrosphingosine | 0.1 g |
| Behenyltrimethylammonium chloride containing 88% AM in a water/isopropanol mixture (15/85), sold under the name | |

-continued

| | | |
|---|---|---|
| Catinal DC 80 (Toho) | | 2 g AM |
| Fragrance, preserving agent | | |
| Water | qs | 100 g |

The pH is adjusted to 5 by addition of hydrochloric acid.

COMPARATIVE EXAMPLES

I Fixing Power

The fixing power obtained by the two formulations A and B below was studied and compared:

Composition A (prior art)

| | | |
|---|---|---|
| Grafted silicone polymer $P_1$ of formula (V) of polymethyl/methylsiloxane structure containing 3-propylthio polymethacrylic acid groups and 3-propylthio polymethyl methacrylate groups | | 5 g AM |
| Tripropylene glycol monomethyl ether (plasticizer) | | 0.5 g |
| Aminomethylpropanol, 100% neutralization of the grafted silicone polymer | qs | |
| 98.5% ethanol | qs | 100 g |

Composition B (invention):

| | | |
|---|---|---|
| Grafted silicone polymer $P_1$ of formula (V) of polymethyl/methylsiloxane structure containing 3-propylthio polymethacrylic acid groups and 3-propylthio polymethyl methacrylate groups | | 5 g AM |
| N-Oleoyldihydrospingosine | | 1 g |
| Tripropylene glycol monomethyl ether (plasticizer) | | 0.5 g |
| Aminoethylpropanol, 100% neutralization of the grafted silicone polymer | qs | |
| 98.5% ethanol | qs | 100 g |

I Procedure

A test for measurement of the strength of the bonds formed between hairs by a hair lacquer is carried out according to the principles of the method described in the article by R. Randall Wickett, John A. Sramek and Cynthia M. Trobaugh in J. Soc. Cosmet. Chem. 43, 169–178 (May/June 1992).

A single strand of hair is taken for each formulation tested. The strand of hair is made into a single loop having a diameter of approximately 2 cm, using a cylindrical support. The hair thus looped is soaked in the formulation and is left to dry under a conditioned atmosphere (20° C. and 50% humidity). The loop fixed with formulation A or B is cut. 2 half-strands of hair linked together by a fixing point are thus obtained.

The ends, located on either side of the fixing point, are fixed to each of the two jaws of an Instron® type machine which measures the tensile force, in Newtons, exerted on the half-strands of hair.

The average force (average of ten tests) $F_A$ and $F_B$ (specific to composition A or B) required to break the fixing point joining the two half-strands of hair and formed by the formulation A or B is measured.

The enhancement afforded by the combination of the grafted silicone polymer $P_1$ and of the ceramide relative to the polymer used alone is determined by calculating the relative variation in the breaking force measured, expressed as a percentage, according to the following formula:

$$(F_B - F_A / F_A) \times 100$$

The results are given in the table below:

| FORMULATION TESTED | BREAKING FORCE EXPRESSED IN - NEWTONS | ENHANCEMENT OF THE FIXING POWER IN % |
|---|---|---|
| A ($P_1$) | 0.09 | — |
| B (Invention) | 0.16 | 77.8% |

II Disentangling

Compositions A and B are packaged in a pump-dispenser bottle.

2 sets of 6 locks of weakly bleached hair weighing 5 g each are used. These locks are washed with a standard shampoo and then dried.

They are suspended vertically, 1.5 g of composition A are sprayed onto each lock of the first series and 1.5 g of composition B are sprayed onto each lock of the second series of locks. The locks are left to dry at room temperature for two hours.

The average force (average of six tests) $F_A$ or $F_B$ (specific to composition A or B) required to disentangle each lock totally is then measured using a dynamometric comb.

The enhancement provided by the combination of the grafted silicone polymer $P_1$ and the ceramide relative to the polymer used alone is determined by calculating the relative variation of the breaking force measured, expressed as a percentage, according to the following formula:

$$(F_B - F_A / F_A) \times 100$$

The results are given in the table below:

| FORMULATION TESTED | BREAKING FORCE EXPRESSED IN NEWTONS | ENHANCEMENT OF THE DISENTANGLING IN % |
|---|---|---|
| A (Comparative) | 22 | — |
| B (Invention) | 12.7 | 42% |

What is claimed is:

1. A cosmetic or dermatological composition comprising, in a cosmetically or dermatologically acceptable medium, at least one grafted silicone polymer comprising:

a polysiloxane portion and a portion including a non-silicone organic chain wherein one of the two portions constitutes the main chain of the polymer, and the other is grafted onto the main chain, and at least one fatty-chain amide corresponding to the general formula (I):

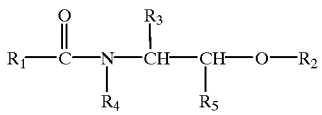

in which:
- R₁ denotes either a linear or branched, saturated or unsaturated, $C_9$–$C_{30}$ hydrocarbon radical, it being possible for this radical to be substituted with one or more hydroxyl groups optionally esterified with a saturated or unsaturated $C_{16}$–$C_{30}$ fatty acid; or a radical R''—(NR—CO)$_n$—R' in which n is equal to 0 or 1, R denotes hydrogen or hydroxyethyl, R' and R'' are hydrocarbon radicals wherein the sum of carbon atoms ranges from 9 to 30, and further in which R' is a divalent radical;
- R₂ denotes a hydrogen atom or a (glycosyl)$_n$, (galactosyl)$_m$ or sulphogalactosyl radical, in which n is an integer ranging from 1 to 4 and m is an integer ranging from 1 to 8;
- R₃ denotes a hydrogen atom or a saturated or unsaturated, $C_{15}$–$C_{27}$ hydrocarbon radical, it being possible for this radical to be substituted with one or more $C_1$–$C_{14}$ alkyl radicals; alternatively R₃ may denote a $C_{15}$–$C_{26}$ α-hydroxyalkyl radical, the hydroxyl group optionally being esterified with a $C_{16}$–$C_{30}$ α-hydroxy acid;
- R₄ denotes a hydrogen atom, a $C_1$–$C_4$ alkyl radical, a saturated or unsaturated $C_{16}$–$C_{27}$ hydrocarbon radical or a group —CH₂—CHOH—CH₂—O—R₆ in which R₆ denotes a $C_{10}$–$C_{26}$ hydrocarbon radical;
- R₅ denotes a hydrogen atom or a mono- or polyhydroxylated $C_1$–$C_4$ hydrocarbon radical.

2. A cosmetic or dermatological composition according to claim 1, wherein said composition is a treatment composition for a keratin substance.

3. A cosmetic or dermatological composition according to claim 2, wherein said keratin substance is human hair.

4. A cosmetic or dermatological composition according to claim 1, wherein R₁ denotes a saturated or unsaturated alkyl radical derived from fatty acids,
R₂ denotes a (galactosyl)$_m$ or sulphogalactosyl radical, and
R₃ denotes a —CH=CH—(CH₂)₁₂—CH₃ group.

5. A cosmetic or dermatological composition according to claim 1, wherein R₁ denotes a saturated or unsaturated alkyl radical derived from $C_{16}$–$C_{22}$ fatty acids,
R₂ denotes a hydrogen atom, and
R₃ denotes a saturated, linear $C_{15}$ radical.

6. A cosmetic or dermatological composition according to claim 1, wherein said at least one grafted silicone polymer is selected from polymers containing a non-silicone organic skeleton grafted with at least one monomer containing at least one polysiloxane and polymers having a polysiloxane skeleton grafted with at least one non-silicone organic monomer.

7. A cosmetic or dermatological composition according to claim 6, wherein said at least one grafted silicone polymer contains a non-silicone organic skeleton comprising an organic main chain formed from at least one organic monomer containing no silicone and further wherein on said organic main chain is grafted, inside said chain and optionally on at least one of the ends of said chain, at least one polysiloxane macromer.

8. A cosmetic or dermatological composition according to claim 7, wherein said at least one non-silicone organic monomer constituting the main chain of said at least one grafted silicone polymer is selected from monomers containing ethylenic unsaturation which are polymerizable via a radical route, monomers which are polymerizable by polycondensation and monomers which involve ring opening.

9. A cosmetic or dermatological composition according to claim 1, wherein said composition comprises at least one silicone grafted polymer comprising:
a) from 0 to 98% by weight of at least one lipophilic monomer (A) of low polarity containing ethylenic unsaturation of low polarity, which is polymerizable via a radical route;
b) from 0 to 98% by weight of at least one polar hydrophilic monomer (B) containing ethylenic unsaturation, which is copolymerizable with said (A) monomer(s);
c) from 0.01 to 50% by weight of at least one polysiloxane macromer (C) of formula (II):

in which:
- X denotes a vinyl group which is copolymerizable with the monomers (A) and (B);
- Y denotes a divalent bonding group;
- R denotes a hydrogen, a $C_1$–$C_6$ alkyl or alkoxy or a $C_8$–$C_{12}$ aryl;
- Z denotes a monovalent polysiloxane unit having a number—average molecular weight of at least 500;
- n is 0 or 1 and m is an integer ranging from 1 to 3;
wherein the percentages by weight are relative to the total weight of monomers (A), (B) and (C) and wherein the sum of a) and b) cannnot constitute 0% by weight relative to the total weight of the monomers.

10. A cosmetic or dermatological composition according to claim 9, wherein said at least one lipophilic monomer (A) is selected from acrylic and methacrylic acid esters of $C_1$–$C_{16}$ alcohols; styrene; polystyrene macromers; vinyl acetate; vinyl propionate; α-methylstyrene; tert-butylstyrene; butadiene; cyclohexadiene; ethylene; propylene; vinyltoluene; acrylic and methacrylic acid esters of 1,1-dihydroperfluoroalkanols and of homologues thereof; acrylic and methacrylic acid esters of ω-hydridofluoroalkanols; acrylic and methacrylic acid esters of fluoroalkylsulphoamido alcohols; acrylic and methacrylic acid esters of fluoroalkyl alcohols; and acrylic and methacrylic acid esters of fluoroether alcohols.

11. A cosmetic or dermatological composition according to claim 9, wherein said at least one lipophilic monomer (A) is selected from n-butyl methacrylate, isobutyl methacrylate, tert-butyl acrylate, tert-butyl methacrylate, 2-ethylhexyl methacrylate, methyl methacrylate, 2-(N-butylperfluorooctanesulphonamido)ethyl acrylate, and 2-(N-methylperfluorooctanesulphonamido)ethyl acrylate.

12. A cosmetic or dermatological composition according to claim 9, wherein at least one polar hydrophilic monomer (B) is selected from: acrylic acid, methacrylic acid, N,N-dimethylacrylamide, dimethylaminoethyl methacrylate, quaternized dimethylaminoethyl methacrylate, (meth) acrylamide, N-t-butylacrylamide, maleic acid, maleic anhydride and demiesters thereof, hydroxyalkyl (meth)acrylates, diallyldimethylammonium chloride, vinylpyrrolidone, vinyl ethers, maleimides, vinylpyridine, vinylimidazole, heterocyclic vinyl polar compounds, styrene sulphonate, allyl alcohol, vinyl alcohol and vinyl caprolactam.

13. A cosmetic or dermatological composition according to claim 12, wherein at least one polar hydrophilic monomer (B) is selected from: acrylic acid, N,N-dimethylacrylamide, dimethylaminoethyl methacrylate, quaternized dimethylaminoethyl methacrylate and vinylpyrrolidone.

14. A cosmetic or dermatological composition according to claim 9, wherein said at least one polysiloxane macromer (C) is selected from compounds corresponding to formula (III):

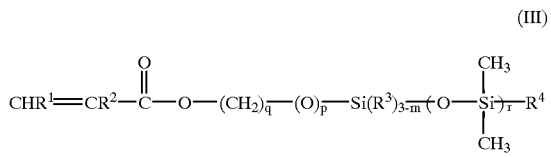

(III)

in which:

$R^1$ is hydrogen or —COOH;

$R^2$ is hydrogen, methyl or —CH$_2$COOH;

$R^3$ is $C_1$–$C_6$ alkyl, alkoxy, or alkylamino, $C_6$–$C_{12}$ aryl or hydroxyl;

$R_4$ is $C_1$–$C_6$ alkyl, alkoxy or alkylamino, $C_6$–$C_{12}$ aryl or hydroxyl;

q is an integer from 2 to 6;

p is 0 or 1;

r is an integer from 5 to 700;

m is an integer from 1 to 3.

15. A cosmetic or dermatological composition according to claim 14, wherein said at least one polysiloxane macromer (C) is selected from compounds corresponding to formula:

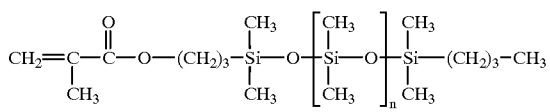

in which:

n is an integer ranging from 5 to 700.

16. A cosmetic or dermatological composition according to claim 1, wherein said at least one grafted silicone polymer contains at least one copolymer which can be obtained by radical polymerization of a monomer mixture comprising:

a) 60% by weight of tert-butyl acrylate;

b) 20% by weight of acrylic acid;

c) 20% by weight of silicone macromer of formula:

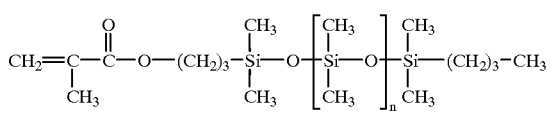

in which:

n is an integer ranging from 5 to 700;

wherein the weight percentages are relative to the total weight of said monomer mixture.

17. A cosmetic or dermatological composition according to claim 1, wherein said at least one grafted silicone polymer contains at least one copolymer which can be obtained by radical polymerization of a monomer mixture comprising:

a) 80% by weight of tert-butyl acrylate;

b) 20% by weight of silicone macromer of formula:

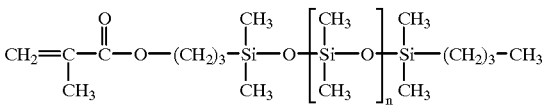

in which:

n is an integer ranging from 5 to 700;

wherein the weight percentages are relative to the total weight of said monomer mixture.

18. A cosmetic or dermatological composition according to claim 6, wherein said polymers containing a non-silicone organic skeleton grafted with at least one monomer containing at least one polysiloxane have a number—average molecular weight ranging from 10,000 to 2,000,000 and a glass transition temperature Tg or a crystalline melting point Tm of at least −20° C.

19. A cosmetic or dermatological composition according to claim 6, wherein said polymers containing a non-silicone organic skeleton grafted with at least one monomer containing at least one polysiloxane are obtained by reactive extrusion of a polysiloxane macromer having a terminal reactive function, with a polyolefin polymer containing reactive groups which can react with the reactive terminal function of said polysiloxane macromer to form a covalent bond resulting in a grafting of said polysiloxane macromer to said polyolefin polymer, said polyolefin polymer forming the skeleton of said polymers.

20. A cosmetic or dermatological composition according to claim 19, wherein said polyolefin polymer is selected from polyethylenes and polymers of ethylene-derived monomers containing reactive functions which can react with the terminal function of the polysiloxane macromer.

21. A cosmetic or dermatological composition according to claim 19, wherein said polyolefin polymer is selected from copolymers of (a) ethylene and/or of ethylene derivatives and of (b) monomers selected from monomers containing a carboxylic function;

monomers containing an acid anhydride function; monomers containing an acid chloride function; monomers containing an ester function; and monomers containing an isocyanate function.

22. A cosmetic or dermatological composition according to claim 19, wherein said at least one polysiloxane macromer is a polysiloxane containing a functionalized group at the end of the polysiloxane chain or close to the end of said chain, said functionalized group being selected from alcohols, thiols, epoxy groups and primary and secondary amines.

23. A cosmetic or dermatological composition according to claim 19, wherein said at least one polysiloxane macromer is a polysiloxane corresponding to formula (IV):

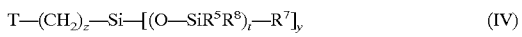

(IV)

in which:

T is selected from NH$_2$, NHR', an epoxy, OH, and SH functions;

$R^5$, $R^6$, $R^7$ and R' each independently denote a $C_1$–$C_6$ alkyl, phenyl, benzyl, $C_6$–$C_{12}$ alkylphenyl or hydrogen;

s is a number ranging from 2 to 100;

t is a number ranging from 0 to 1000; and y is a number ranging from 1 to 3.

24. A cosmetic or dermatological composition according to claim 1, wherein said composition comprises at least one grafted silicone polymer containing a polysiloxane main chain grafted with at least one non-silicone organic monomer, wherein on said polysiloxane main chain is grafted, inside said main chain and optionally on at least one of its ends, said at least one non-silicone organic monomer.

25. A cosmetic or dermatological composition according to claim 24, wherein said at least one grafted silicone polymer can be obtained by radical copolymerization between at least one non-silicone organic monomer having ethylenic unsaturation selected from anionic and hydrophobic monomers, and, at least one polysiloxane having in its chain at least one functional group capable of reacting with said ethylenic unsaturation of said at least one non-silicone organic monomer.

26. A cosmetic or dermatological composition according to claim 25, wherein said non-silicone anionic organic monomer is selected from linear and branched, unsaturated carboxylic acids optionally partially and totally neutralized in the form of a salt.

27. A cosmetic or dermatological composition according to claim 25, wherein said anionic organic monomer is selected from acrylic acid, methacrylic acid, maleic acid, maleic anhydride, itaconic acid, fumaric acid, crotonic acid, alkali-metal salts of said acids, alkaline-earth metal salts of said acids and ammonium salts of said acids.

28. A cosmetic or dermatological composition according to claim 25, wherein said non-silicone hydrophobic organic monomer is selected from acrylic acid esters of alkanol and methacrylic acid esters of alkanol.

29. A cosmetic or dermatological composition according to claim 28, wherein said alkanol is $C_1$–$C_{18}$.

30. A cosmetic or dermatological composition according to claim 29, wherein said alkanol is $C_1$–$C_{12}$.

31. A cosmetic or dermatological composition according to claim 27, wherein said non-silicone hydrophobic organic monomer is selected from isooctyl (meth)acrylate, isononyl (meth)acrylate, 2-ethylhexyl (meth)acrylate, lauryl (meth) acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth) acrylate.

32. A cosmetic or dermatological composition according to claim 24, wherein said at least one grafted silicone polymer comprises, on the main silicone chain, at least one non-silicone organic group of anionic nature obtained by the radical (homo)-polymerization of at least one non-silicone anionic unsaturated carboxylic acid monomer, partially or totally neutralized in the form of a salt.

33. A cosmetic or dermatological composition according to claim 24, wherein said at least one grafted silicone polymer is selected from silicone polymers containing in their structure at least one unit of formula (V):

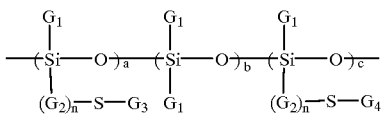

in which:

the radicals $G_1$ independently represent hydrogen, a $C_1$–$C_{10}$ alkyl radical or a phenyl radical;

the radicals $G_2$ independently represent a divalent $C_1$–$C_{10}$ alkylene group;

$G_3$ represents a polymer residue resulting from the (homo)-polymerization of at least one anionic monomer containing ethylenic unsaturation;

$G_4$ represents a polymer residue resulting from the (homo)-polymerization of at least one hydrophobic monomer containing ethylenic unsaturation;

m and n are equal to 0 or 1;

a is an integer ranging from 0 to 50;

b is an integer ranging from 10 to 350;

c is an integer ranging from 0 to 50;

with the proviso that one of a and c is not 0.

34. A cosmetic or dermatological composition according to claim 33, wherein said at least one unit of formula (V) has at least one of the following characteristics:

the radicals $G_1$ denote a $C_1$–$C_{10}$ alkyl radical;

n is 1;

the radicals $G_2$ represent a divalent $C_1$–$C_3$ radical;

$G_3$ represents a polymeric residue resulting from the (homo)-polymerization of at least one carboxylic acid monomer containing ethylenic unsaturation;

$G_4$ represents a polymeric residue resulting from the (homo)-polymerization of at least one ($C_1$–$C_{10}$) alkyl (meth)acrylate monomer.

35. A cosmetic or dermatological composition according to claim 33, wherein said at least one unit of formula (V) simultaneously has the following characteristics:

the radicals $G_1$ denote a methyl radical;

n is not zero the radicals $G_2$ represent a propylene radical;

$G_3$ represents a polymeric residue resulting from the (homo)polymerization of at least one monomer selected from acrylic acid and methacrylic acid; and $G_4$ represents a polymeric residue resulting from the (homo)-polymerization of at least one monomer selected from isobutyl and methyl (meth)acrylate monomers.

36. A cosmetic or dermatological composition according to claim 24, wherein said at least one grafted silicone polymer has a number-average molecular mass ranging from 10,000 to 1,000,000.

37. A cosmetic or dermatological composition according to claim 36, wherein said at least one grafted silicone polymer has a number-average molecular mass ranging from 10,000 to 100,000.

38. A cosmetic or dermatological composition according to claim 1, wherein said at least one grafted silicone polymer is present in a concentration ranging from 0.01 to 20% by weight relative to the total weight of the composition.

39. A cosmetic or dermatological composition according to claim 38, wherein said at least one grafted silicone polymer is present in a concentration ranging from 0.1 to 15% by weight relative to the total weight of the composition.

40. A cosmetic or dermatological composition according to claim 39, wherein said at least one grafted silicone polymer is present in a concentration ranging from 0.5 to 10% by weight relative to the total weight of the composition.

41. A cosmetic or dermatological composition according to claim 1, wherein said at least one fatty-chain amide is selected from:
N-linoleoyldihydrosphingosine,
N-oleoyidihydrosphingosine,
N-palmitoyldihydrosphingosine,
N-stearoyldihydrosphingosine, and
N-behenoyldihydrosphingosine.

42. A cosmetic or dermatological composition according to claim 1, wherein said at least one fatty-chain amide is selected from: bis(N-hydroxyethyl-N-cetyl)malonamide, cetylic acid N-(2-hydroxyethyl)-N-(3-cetyloxy-2-hydroxypropyl)amide and N-docosanoyl-N-methyl-D-glucamine.

43. A cosmetic or dermatological composition according to claim 1, wherein said at least one fatty-chain amide is present in a concentration ranging from 0.0001 to 20% by weight relative to the total weight of the composition.

44. A cosmetic or dermatological composition according to claim 43, wherein said at least one fatty-chain amide is present in a concentration ranging from 0.001 to 10% by weight relative to the total weight of the composition.

45. A cosmetic or dermatological composition according to claim 44, wherein said at least one fatty-chain amide is present in a concentration ranging from 0.005 to 3% by weight relative to the total weight of the composition.

46. A cosmetic or dermatological composition according to claim 1, wherein said composition further comprises at least one additive selected from: thickeners, fatty acid esters, fatty acid esters of glycerol, silicones, surfactants, fragrances, preserving agents, sunscreens, proteins, vitamins, different polymers, and plant, animal, mineral and synthetic oils.

47. A cosmetic or dermatological composition according to claim 1, wherein said cosmetically or dermatologically acceptable medium comprises water or a mixture of water and at least one cosmetically acceptable solvent.

48. A cosmetic or dermatological composition according to claim 47, wherein said at least one cosmetically acceptable solvent is selected from monoalcohols, polyalcohols, glycol ethers and fatty acid esters.

49. A cosmetic or dermatological composition according to claim 1, wherein said composition is in the form of a gel, a milk, a cream, a thickened lotion or a mousse.

50. A cosmetic or dermatological composition according to claim 1, wherein said composition is a hair product.

51. A cosmetic or dermatological composition according to claim 50, wherein said hair product is selected from shampoos, rinse-out or leave-in hair products, to be applied before or after shampooing, dyeing, bleaching, permanent-waving or straightening the hair.

52. A cosmetic or dermatological composition according to claim 1, wherein said composition is packaged in the form of a vaporizer, a pump-dispenser bottle or an aerosol container.

53. A cosmetic or dermatological composition according to claim 1, wherein said at least one grafted silicone polymer is dissolved in the cosmetically or dermatologically acceptable medium or is in the form of an aqueous dispersion of particles.

54. A non-therapeutic process for treating a keratin substance comprising applying a composition according to claim 1 to said keratin substance and then optionally rinsing with water.

55. A non-therapeutic process according to claim 54, wherein said keratin substance is human hair.

* * * * *

UNITED STATES PATENT AND TRADEMARK OFFICE
CERTIFICATE OF CORRECTION

PATENT NO.: 6,165,444

DATED: December 26, 2000

INVENTORS: Claude DUBIEF; Daniele CAUWET-MARTIN; and Christine DUPUIS

It is hereby certified that errors appear in the above-identified patent and that said Letters Patent is hereby corrected as shown below:

IN THE ABSTRACT:

Front page, line 9, change "an" to --and--.

IN THE SPECIFICATION:

Col. 7, line 45, FORMULA (V) change "$(G_2)_n$" (second occurrence) to --$(G_2)_m$--.

IN THE CLAIMS:

Claim 18, col. 16, line 17, change "number—average" to --number-average--.

Claim 33, col. 18, in FORMULA (V), change "$(G_2)_n$" (second occurrence) to --$(G_2)_m$--.

Signed and Sealed this

Twenty-ninth Day of May, 2001

Attest:

NICHOLAS P. GODICI

Attesting Officer

Acting Director of the United States Patent and Trademark Office